(12) United States Patent
Finkel

(10) Patent No.: US 11,986,315 B2
(45) Date of Patent: May 21, 2024

(54) APPARATUS AND METHOD FOR THE NON-INVASIVE DETECTION OF TETRAHYDROCANNABINOL USE AND IMPAIRMENT

(71) Applicant: CHILDREN'S NATIONAL MEDICAL CENTER, Washington, DC (US)

(72) Inventor: Julia C. Finkel, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 899 days.

(21) Appl. No.: 16/963,457

(22) PCT Filed: Jan. 15, 2019

(86) PCT No.: PCT/US2019/013683
§ 371 (c)(1),
(2) Date: Jul. 20, 2020

(87) PCT Pub. No.: WO2019/143627
PCT Pub. Date: Jul. 25, 2019

(65) Prior Publication Data
US 2021/0045680 A1 Feb. 18, 2021

Related U.S. Application Data

(60) Provisional application No. 62/619,466, filed on Jan. 19, 2018.

(51) Int. Cl.
*G06T 7/70* (2017.01)
*A61B 3/00* (2006.01)
(Continued)

(52) U.S. Cl.
CPC .......... *A61B 5/4845* (2013.01); *A61B 3/0041* (2013.01); *A61B 3/112* (2013.01);
(Continued)

(58) Field of Classification Search
CPC ..................... G06T 7/70; G06T 7/0014; G06T 2207/10016; G06T 2207/30041;
(Continued)

(56) References Cited

U.S. PATENT DOCUMENTS 5,692,502 A    12/1997  Alpert
9,357,966 B1 *  6/2016  Cohen ................... G16H 40/63
(Continued)

FOREIGN PATENT DOCUMENTS

JP    2017-529891 A    10/2017

OTHER PUBLICATIONS

"Alessandro Amodio, Automatic Detection of Driver Impairment Based on Pupillary Light Reflex, 2018, IEEE, pp. 1-11" (Year: 2018).*

(Continued)

*Primary Examiner* — Shefali D Goradia
*Assistant Examiner* — D J Dhooge
(74) *Attorney, Agent, or Firm* — Oblon, McClelland, Maier & Neustadt, L.L.P.

(57) ABSTRACT

The present disclosure is related to a method and apparatus for determining THC usage of a person. The present disclosure describes acquiring a video sequence, of an eye of a patient, the video sequence being a plurality of video frames, determining a frequency spectrum from a pupillary data of the video sequence, and determining, based on the frequency spectrum, the physiological characteristic or drug of use of the patient. In an embodiment, at least one frequency can be probed based on which physiological characteristic is being explored. For example, the physiological characteristic can (Continued)

be Δ#-tetrahydrocannabinol, and the at least one frequency probed can be selected to be specific to Δ#-tetrahydrocannabinol.

15 Claims, 7 Drawing Sheets

(51) Int. Cl.
    *A61B 3/11*     (2006.01)
    *A61B 5/00*     (2006.01)
    *G06T 7/00*     (2017.01)
    *G16H 10/20*     (2018.01)
    *G16H 15/00*     (2018.01)
    *G16H 30/40*     (2018.01)
    *G16H 50/20*     (2018.01)
    *G16H 50/30*     (2018.01)
    *G16H 50/70*     (2018.01)
    *G16H 70/40*     (2018.01)
    *G16H 70/60*     (2018.01)

(52) U.S. Cl.
    CPC .............. *G06T 7/0014* (2013.01); *G06T 7/70* (2017.01); *G16H 10/20* (2018.01); *G16H 15/00* (2018.01); *G16H 30/40* (2018.01); *G16H 50/20* (2018.01); *G16H 50/30* (2018.01); *G16H 50/70* (2018.01); *G16H 70/40* (2018.01); *G16H 70/60* (2018.01); *G06T 2207/10016* (2013.01); *G06T 2207/30041* (2013.01)

(58) Field of Classification Search
    CPC ........ G16H 70/60; G16H 15/00; G16H 50/30; G16H 50/70; G16H 50/20; G16H 70/40; G16H 30/40; G16H 10/20; A61B 3/112
    See application file for complete search history.

(56) References Cited

U.S. PATENT DOCUMENTS

| | | |
|---|---|---|
| 9,414,745 B2 | 8/2016 | Neice |
| 2002/0024633 A1* | 2/2002 | Kim ...................... A61B 3/112 382/117 |
| 2009/0213329 A1* | 8/2009 | Kandel .................. A61B 3/112 351/246 |
| 2009/0271011 A1* | 10/2009 | Hyde ..................... G16H 40/67 700/28 |
| 2010/0136537 A1* | 6/2010 | Swaroop ............ C12N 15/8509 435/6.14 |
| 2014/0268047 A1* | 9/2014 | Hirsh ..................... A61B 3/112 351/246 |
| 2015/0116665 A1 | 4/2015 | Finkel |
| 2016/0192838 A1 | 7/2016 | Hirsh |
| 2017/0007119 A1 | 1/2017 | Cornsweet et al. |
| 2017/0100061 A1* | 4/2017 | Finkel ................... A61B 5/103 |

OTHER PUBLICATIONS

Extended European Search Report dated Jul. 9, 2021 in European Patent Application No. 19741772.8, 9 pages.
Japanese Office Action dated Sep. 13, 2022 in Japanese Patent Application No. 2020-539856, citing document 15 therein, 3 pages.
International Search Report and Written Opinion dated Jul. 5, 2019 in PCT/US2019/013683 filed on Jan. 15, 2019.
Indian Office Action dated Jun. 24, 2022 in Indian Patent Application No. 202017029902, 7 pages.
Combined Chinese Office Action and Search Report dated Nov. 7, 2023, in corresponding Chinese Patent Application No. 201980011179.1 (with English Translation). 16 pages.
Office Action dated Oct. 16, 2023, in corresponding Korean Patent Application No. 10-2020-7023188, 5 pages.
Australian Examination Report No. 1 dated Nov. 7, 2023 in Australian Patent Application No. 2019209329, citing references 1 and 24-26 therein, 6 pages.
Bokoch et al., "Fentanyl, an agonist at the mu opioid receptor, depresses pupillary unrest", Autonomic Neuroscience: Basic and Clinical, vol. 189, 2015, pp. 68-74.
Heishman et al., "Laboratory Validation Study of Drug Evaluation and Classification Program: Ethanol, Cocaine, and Marijuana", Journal of Analytical Toxicology, vol. 20, Oct. 1996, pp. 468-483 (with cover page).
Adler et al., Drug Recognition Expert (DRE) Validation Study, Final Report to Governor's Office of Highway Safety, State of Arizona, Jun. 4, 1994, 105 pages.
Office Action dated Mar. 15, 2024, issued in counterpart EP Application No. 19 741 772.8, (7 pages).

\* cited by examiner

APPARATUS AND METHOD FOR THE NON-INVASIVE DETECTION OF TETRAHYDROCANNABINOL USE AND IMPAIRMENT

CROSS-REFERENCE TO RELATED APPLICATIONS

The present application claims priority to U.S. Provisional Application No. 62/619,466, filed Jan. 19, 2018, the teaching of which is hereby incorporated by reference in its entirety for all purposes. Further, this application is related to U.S. Patent Application No. 2015/0116665, filed Sep. 19, 2014, U.S. Patent Application No. 2017/0100061, filed Oct. 11, 2016, and U.S. Pat. No. 9,326,725, filed Mar. 30, 2011, the contents of which are incorporated herein by reference.

BACKGROUND

Field of the Disclosure

The present disclosure is related to drug use and/or physiologic impairments and their impact on pupillary hippus. Specifically, the present disclosure describes the utilization pupillometry for the detection of $\Delta^9$-tetrahydrocannabinol use and impairment based upon parameters of the pupillary light reflex.

Description of the Related Art

Pupillary control requires a complex physiology involving numerous neuronal pathways. Pupillary behavior, therefore, provides a window to the integrity and functionality of these neuronal pathways. Furthermore, pupillary behavior, as indicated by contraction and dilation of the iris by the sphincter and dilator muscles, can reflect alterations or abnormalities in the metabolism or the structure of the central nervous system. This connection to the central nervous system makes the determination and identification of pathologies critical in clinical and experimental settings, and suggests that evaluation of pupillary behavior may provide a mechanism for rapid detection and diagnosis of pathologies.

Pupil assessment, however, while being a routine practice in medical care and used in a variety of settings ranging from first responders to intensive care units, is most commonly performed using a penlight and visual, subjective observation. This subjective approach is hindered by inter-operator variability attributed to operator expertise and, though an easy assessment method, fails to provide granular data. For instance, the information generated by the penlight approach can be limited to gross pupil features such as the presence or absence of light reflex and a rough estimation of pupil size and symmetry. As would be expected, subtle changes that may be important tools in tracking clinical conditions such as brain trauma or viability following cardiac or pulmonary arrest cannot be assessed.

Even when more resolved methods have been employed, such as pupillometers, broad acceptance and deployment has been slow. These methods, though they can be used to evaluate pupillary size and reactivity, can be costly and can require stand-alone equipment that provides raw data without interpretation, necessitating the introduction of a trained professional to evaluate the data, synthesize the information, and provide proper guidance to a consumer regarding appropriate interventions.

Therefore, effective and convenient evaluation of pupillary behavior, promising to provide pupillary measurements that can be used to, among other things, monitor drug use, drug abuse, drug tolerance, and drug hyperalgesia, is needed, in particular as related to $\Delta^9$-tetrahydrocannabinol use and impairment.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

According to an embodiment, the present disclosure is related to an apparatus for evaluation of a pupillary hippus of a patient.

In an embodiment, the present disclosure is further related to an apparatus for evaluation of a pupillary hippus of a patient, comprising a display, and processing circuitry configured to transform experimental data of the pupillary hippus of the patient and reference data via frequency-based transformation, calculate a first parameter of one or more selected parameters based upon the transformed experimental data of the pupillary hippus of the patient, calculate, based upon the transformed reference data, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of $\Delta^9$-tetrahydrocannabinol as the biologically-active target.

In an embodiment, the present disclosure is further related to an apparatus for evaluation of a pupillary hippus of a patient, comprising a display, and processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of $\Delta^9$-tetrahydrocannabinol as the biologically-active target.

In an embodiment, the present disclosure is further related to an apparatus for evaluation of a pupillary hippus of a patient, comprising processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on a display and based upon the determination, the evaluation of the pupillary hippus of the patient.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
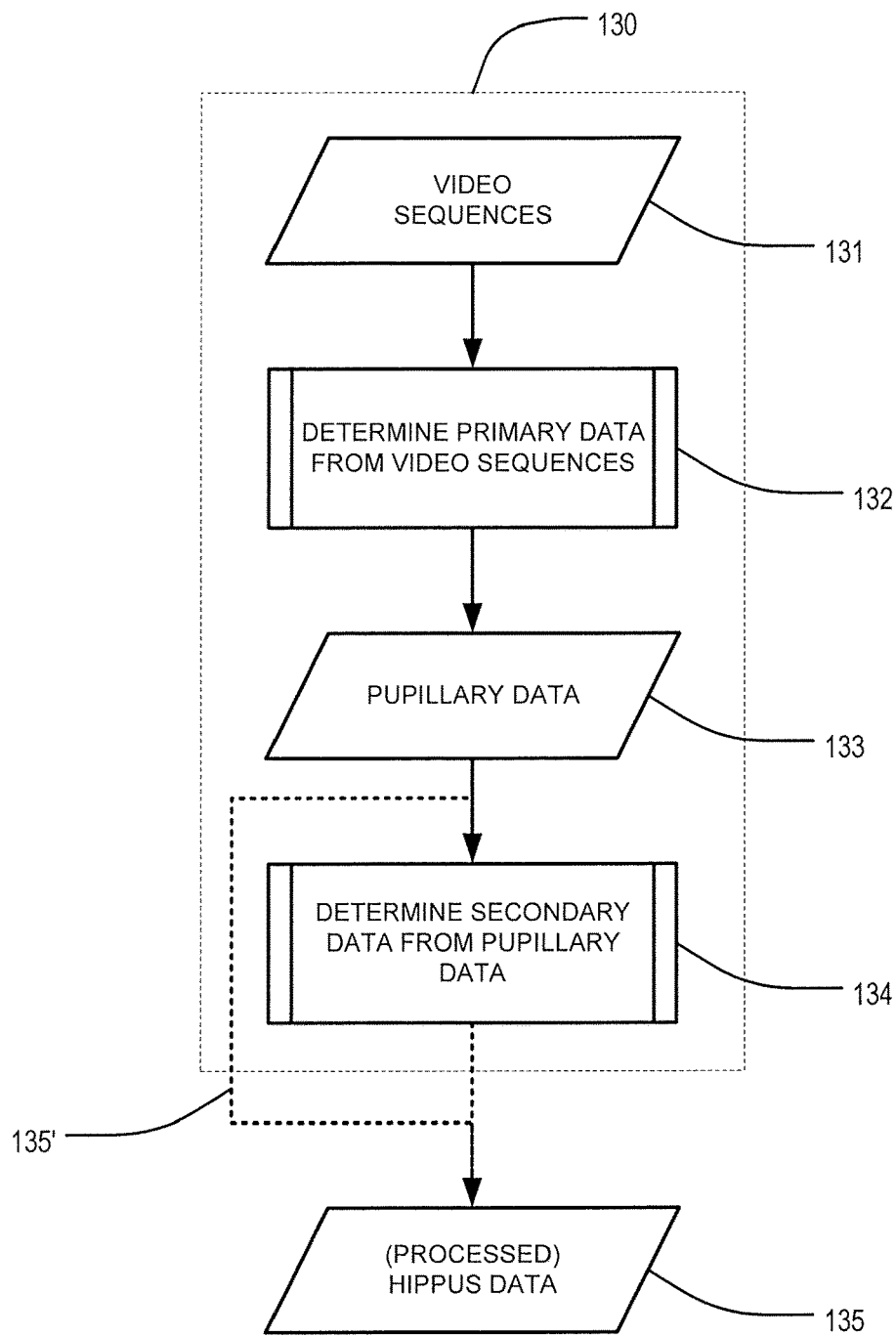
FIG. 1 is a flow diagram describing processing of acquired data, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

According to an embodiment, the present disclosure describes a method and apparatus that allows clinicians, health care professionals, and consumers, in cases, to evaluate, precisely and objectively, the dynamic pupillary oscillations that, in part, define pupillary behavior. Moreover, these dynamic pupillary oscillations can be used in conjunction with a variety of pathology-specific algorithms, the pathology-specific algorithms being specific to different drug signatures and physiologic conditions, in order to identify pathologies therefrom. For example, the pathology-specific algorithm can be directed to the detection and determination of $\Delta^9$-tetrahydrocannabinol (THC) use and impairment.

According to an exemplary embodiment of the present disclosure, evaluation of dynamic pupillary oscillations can be performed by an apparatus, or a pupillometry device, that combines an imaging apparatus having an imaging sensor, such as an infrared camera or CMOS sensor within housing, and a display apparatus which can be a smartphone or a dedicated display module. In an embodiment, the imaging apparatus and the display apparatus may be both contained within a smartphone or similar mobile terminal. Connection with the display will enable a software application to objectively generate comparative information of the dynamic pupillary oscillations such that it can facilitate understanding of the comparative information. To this end, the above-described apparatus can be a screening tool and software applications thereof can be algorithms and methods developed to specifically address a variety of clinical situations, such as the detection of THC use and consumer impairment therefrom. These software applications enable objective measurement of the dynamic pupillary behavior in, for example, the clinical setting and can be stored within a memory of the smartphone or the apparatus.

According to an embodiment, the above-described apparatus of the present disclosure can implement a method in combination with additionally-described hardware. For example, such hardware can be a chamber constructed to adapt a smartphone to a patient's, or a user's, face. To facilitate data acquisition, the exemplary imaging apparatus, or infrared camera, can be adaptable, via the additionally-described hardware, to ergonomically form to a patient's face to enable accurate pupil assessment. Moreover, this allows implementation of the method in myriad environments, wherein it can be performed by a ubiquitous device. The method, in an embodiment, can be performed by processing circuitry configured to control the imaging apparatus of the smartphone or other device in order to acquire video sequences of an eye of a person. Such video sequences can be acquired, for example, at 100 frames per second, though it should be appreciated that other frame rates can be used in order to obtain the pupillary video sequences.

During real-world implementation, the above-described apparatus and method thereof, according to an exemplary embodiment, can provide rapid access to patient data that can be important tools in a variety of clinical situations. By comprising an integration-ready chamber that is adjustable to a patient's face with a dedicated display for the collected information, in an embodiment, convenient and mobile acquisition of patient pupillary data can be realized and analysis expediently performed. Enhancing the adaptability of the approach, specific algorithms can be deployed in order to interpret the acquired patient pupillary data, adjustable to different clinical situations, thereby allowing broad use and access by a variety of professionals and laypersons, including, but not limited to, medical professionals.

Among multiple applications, the assessment of pupillary oscillations can be applied to the identification of drug use. The identification of drug use presents one of the greatest opportunities for broader use of pupillometry. Drugs confer specific effects on the autonomic nervous system, thereby affecting the pupil, and pupillary oscillations, directly. Examination of pupillary oscillations, known as hippus, using spectral analysis, for example, renders specific, attributable frequency responses. Drug usage changes the spectral profile of hippus in specific, attributable ways, and different drug classes impact the this profile in unique ways. For example, THC use uniquely impacts parameters of the spectral profile of hippus, specifically, and the pupillary light reflex, more generally. The apparatus and method of the present disclosure, as introduced above, may be an important tool in understanding drug usage correlations and evaluating patients for drug use status, particularly as related THC use and impairment.

Additionally, and according to an embodiment, the apparatus and method of the present disclosure may be employed in the evaluation of the function of the autonomic nervous system in the context of a physiologic condition. Pupillary oscillations are known to vary due to abnormal activity in the autonomic nervous system, such as the presence of a dysautonomia. Therefore, the function of the autonomic nervous system and abnormal activities thereof may be evaluated via the apparatus and method of the present disclosure, thus render the present disclosure an important tool in evaluating patients for the presence of specific physiologic conditions.

With reference now to the Figures and as described above, the present disclosure, according to an embodiment, is related to an apparatus, and a method thereof, of determining the presence of a biologically-active compound, a drug, or a physiologic perturbation in a patient. Specifically, embodiments of the present disclosure described herein are related to an apparatus and method of determining THC presence and consumer impairment.

Briefly, the method includes, for instance, the steps of: (1) acquiring a video sequence of an eye of a patient, the video sequence including a plurality of video frames, (2) detecting and measuring pupil dimensions in each of the plurality of video frames of the video sequence, wherein the dimensions of the time-based pupil size form pupillary oscillations of the patient, (3) determine, using local or remote processing circuitry, based upon the pupillary oscillations, a frequency spectrum of the detected and measured pupil dimensions over time, and (4) determining, using the processing circuitry and based upon a band power of the frequency spectrum (i.e. area under the curve), the presence of a drug or a physiologic condition of the patient and, in particular, THC use and impairment.

Referring now to FIG. 1, and with additional details as to the above, the method can comprise data processing 130 that includes first, as outlined in FIG. 1, the acquisition of a video sequence 131 of an eye of a patient, the video including a plurality of video frames. Following acquisition 131, primary data such as, for instance, pupillary dimensions and pupillary oscillations therefrom, can be determined for each of the plurality of video frames in the video sequence of the eye of the patient 132.

Figure 2:
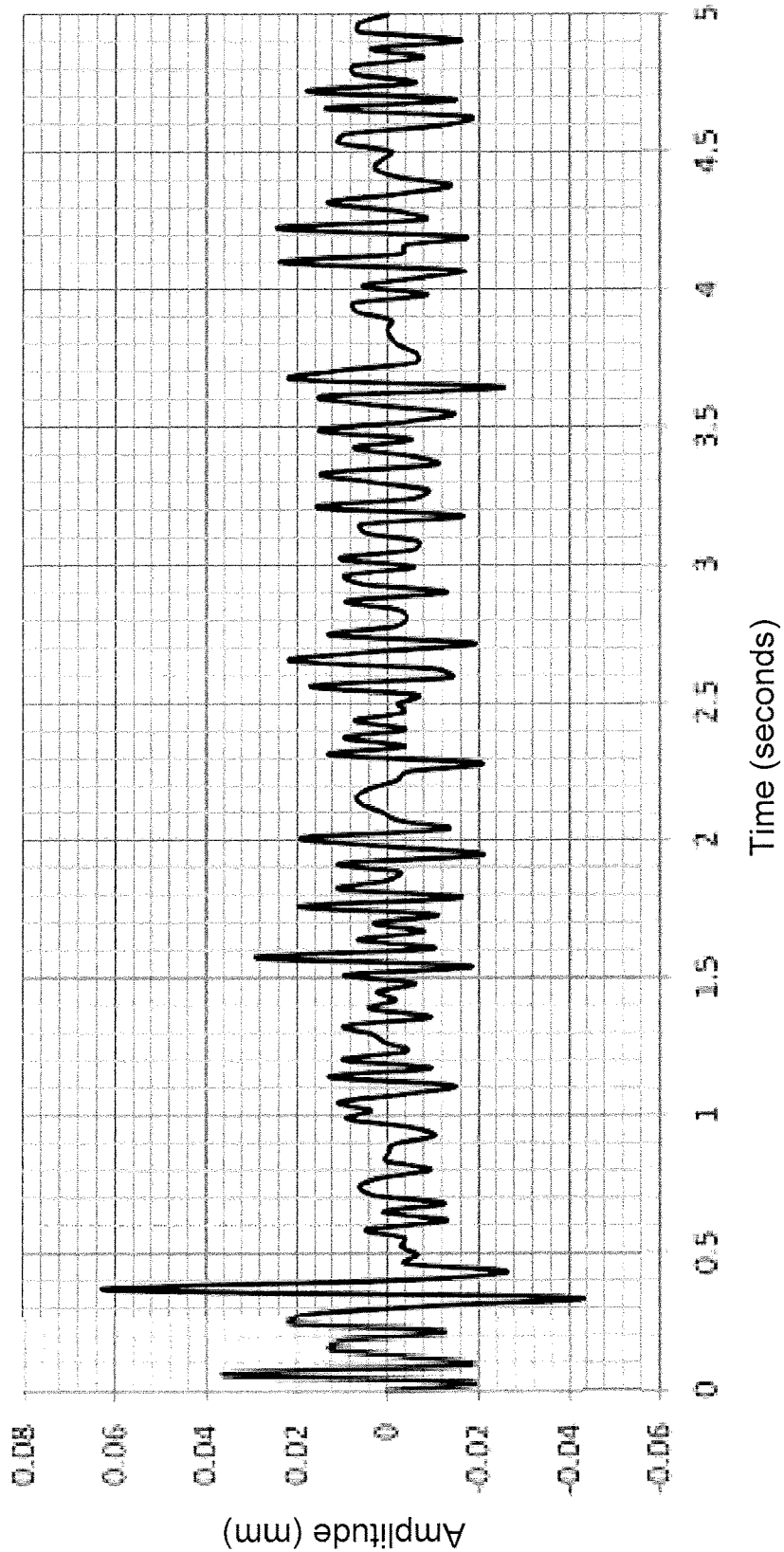
FIG. 2 is a graphical representation of pupillary oscillations as isolated prior to spectral analysis, according to an exemplary embodiment of the present disclosure.

According to an embodiment, FIG. 2 is a graphical illustration of pupillary data of an isolated hippus isolated prior to spectral analysis. Specifically, amplitude pupillary oscillations over a 5-second period of a pupillary light reflex of are shown.

Returning now to FIG. 1, the data 133 that defines the pupillary oscillations can then be mined, via processing circuitry either local or remote, to determine, for instance, secondary data 134 that can include a frequency spectrum of the pupillary oscillations over time. The frequency spectrum determined to be secondary data 134 of the pupillary data 133 can then be provided as processed hippus data 135 to a method of the present disclosure for evaluating the newly processed data. Alternatively, or in combination with, the pupillary data can forgo additional data manipulation 135' and can immediately define processed hippus data 134.

With regard to implementation of the method of the present disclosure, the processed hippus data 134 can be accessible during run time of the method, wherein the processed hippus data 134 from an experimental hippus and processed hippus data 134 from a reference hippus can be used to determine the presence of, among others, a biologically-active compound, a drug, or other physiologic perturbation of the patient. For instance, this can be a determination of the presence and/or level of THC-induced impairment based on a band power calculated from the frequency spectrum.

Different applications, such as detection of drug use, or, for instance, presence of THC or THC-induced impairment, or detection of a medical condition or physical perturbation can take into account different pupillometric measures and different amounts of weight or different ways of processing the pupillometric measures.

The method of FIG. 1 can be initiated by, for example, (1) during the initial processing of the video sequences 132, localizing, in a first frame among the plurality of frames, a center of the pupil and two points on a boundary of the pupil and the iris, (2) generating, using the processing circuitry, a mask image corresponding to an expected location of the iris based on said localizing, said mask image including a plurality of pixels, and (3) determining the pupillary dimensions (i.e. primary data), and pupillary oscillations therefrom, based on the generated mask image.

The acquired video sequence can be processed, as above, by a processor in an attachable device such as, among others, a smartphone or cloud based processing. Although a smartphone, in context of the processing circuitry above, is described herein and has been described previously, as evidenced by US 2015/0116665 A1 and incorporated herein by reference, it can be appreciated that any processor, including an external processor or cloud-based processing circuitry, can be used to process the acquired video sequence.

Further to the above, the acquired video sequence can include pupillary reaction to, for instance, a flash of light. In order to create this reaction, or pupillary light reflex, a flash of light, according to standardized lighting conditions, can be provided by the flashlight of the aforementioned smartphone or similar mobile device.

Pupillary oscillations and/or reactions to light, as described above, can reflect the activity of the autonomic nervous system. For instance, in exhibiting the pupillary light reflex and reflecting the integrity of the autonomic nervous system, constriction, or miosis, occurs in response to the flash of light as a result of increased parasympathetic tone while dilation, or mydriasis, reflects increased sympathetic tone. The pupillary light reflex can be evaluated via the method, and apparatus thereof, of the present disclosure, wherein higher frequency activation occurs with increased sympathetic tone and lower frequency activation occurs from increased parasympathetic tone. Applied in the real world, pupillary oscillations may be impacted by the activity of certain biologically-active compounds, drugs, of physiological conditions that interact with receptors of the autonomic nervous system, impacting either sympathetic or parasympathetic responses.

According to an embodiment, a variety of pupillometric measures can be evaluated from pupillary data following initial video sequence processing 132 such that, in combination with secondary data 134 including frequency spectra, patient response profiles can be better characterized. There are at least six pupillometric measures used in the generation of algorithms that can aid in the determination of a physiological characteristic such as, for example, usage of drugs or a medical condition. At least two of the pupillometric measures are static measures and can include baseline pupil size and maximally constricted size. These measures can be used to generate, for example, constriction amplitude. As introduced above, the baseline pupil size can be found before the flash of light and the maximally constricted size can be determined after the flash of light. At least four of the pupillometric measures can be dynamic measures and can be dynamic responses to the flash of light, including velocity of constriction (average constriction velocity and maximum constriction velocity), latency of constriction, and velocity of re-dilation. As related to the detection and identification of drug use or pathologic condition, the various parameters of the pupillary light reflex are impacted in a predictable way by various drugs and medical conditions. Any of the at least six pupillometric measures can be suitable metrics according to the application of the measurement. As the application changes, such as the detection of specific drug use or detection of a specific medical condition, different pupillometric measures and different amounts of weight or different ways of processing in pupillometric measures can be considered, as appropriate.

Figure 3:
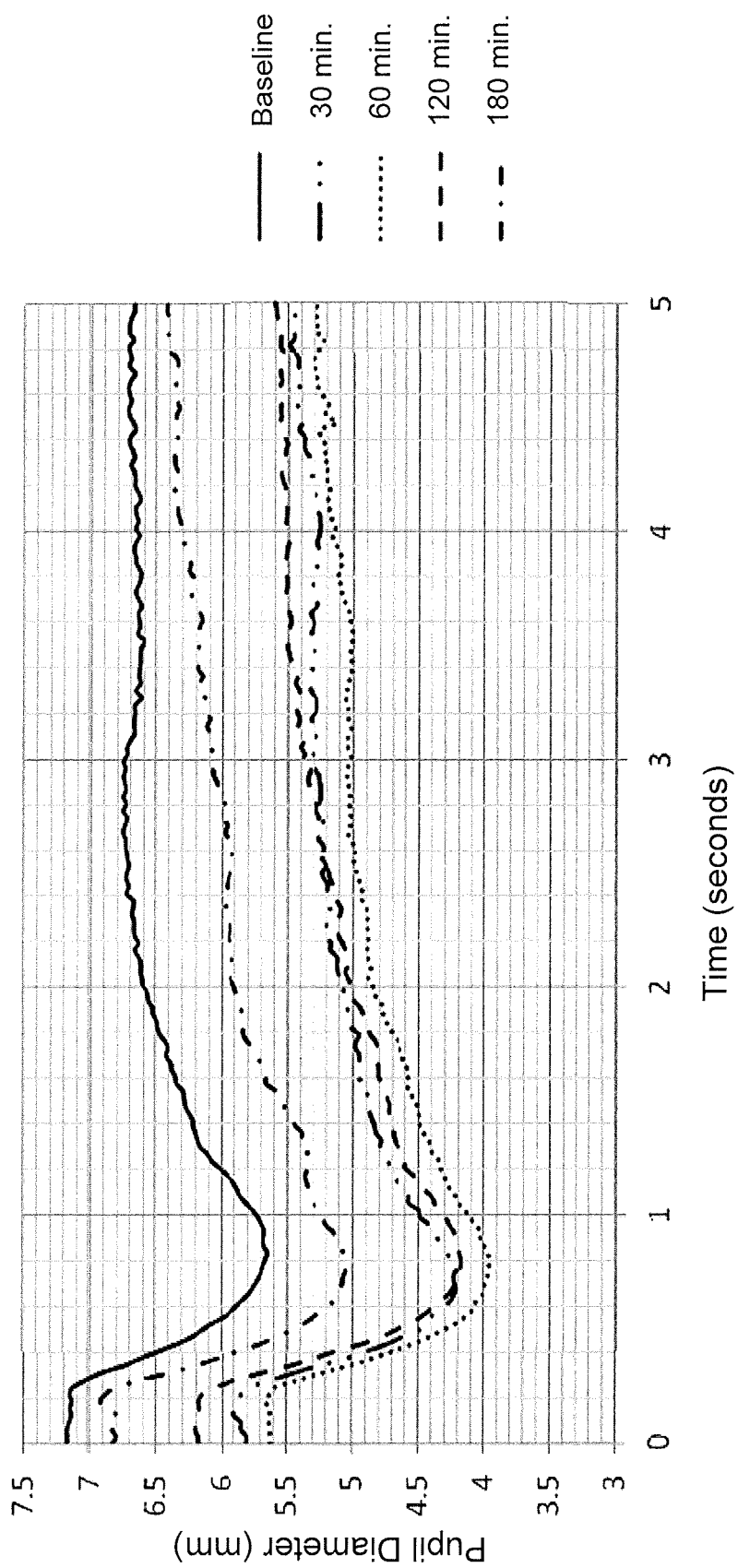
FIG. 3 is a graphical representation of evaluation of a pupillary light reflex after inhalation of THC, according to an exemplary embodiment of the present disclosure.

Further to the above, FIG. 3 is a graphical illustration of the influence of THC on pupillary light reflex. As illustrated, the pupillary light reflex of an individual is inhibited to varying levels at 30 minutes, 60 minutes, 120 minutes, and 180 minutes after inhalation of 24 mg of THC, a variation that can parsed out with the method of the present disclosure to aid in, for example, identification of impairment and/or level of impairment.

Figure 4:
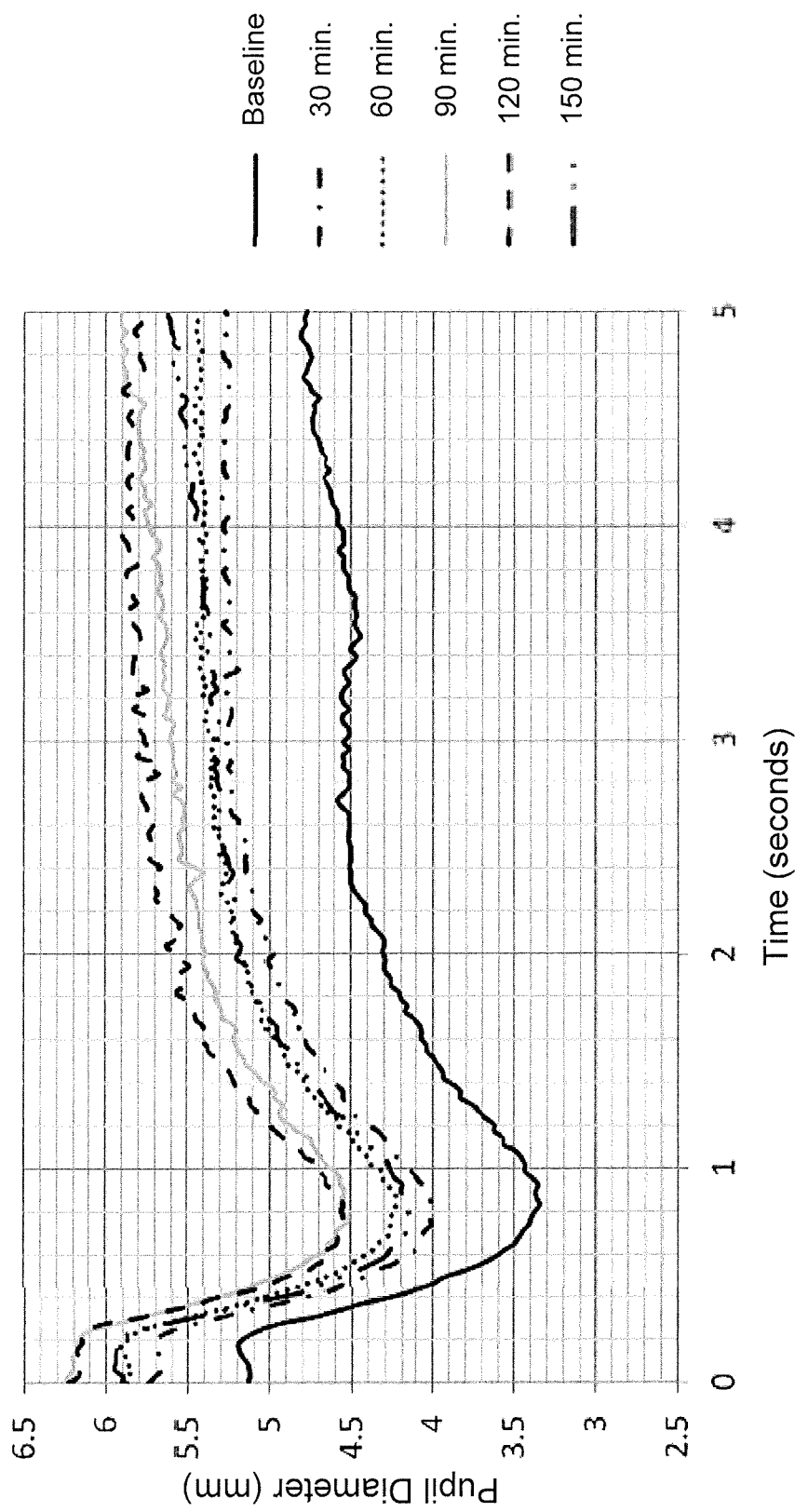
FIG. 4 is a graphical representation of evaluation of a pupillary light reflex after inhalation of THC by a cannabis-tolerant individual, according to an exemplary embodiment of the present disclosure.

Additionally, a similar but opposite response is observed in FIG. 4, a graphical illustration of the influence of THC on pupillary light reflex of a cannabis-tolerant individual. As shown, the pupillary light reflex of a cannabis-tolerant individual is inhibited to varying levels at 30 minutes, 60 minutes, 90 minutes, 120 minutes, and 150 minutes after the inhalation of THC, a variation that can parsed out with the method of the present disclosure to aid in, for example, identification of impairment and/or level of impairment.

According to an embodiment, the above-described pupillometric measures, or parameters, can include at least one of a plurality of additional parameters including a maximum pupil size, a maximum change in size of the pupil, a maximum velocity of re-dilation of the pupil, a mean velocity of re-dilation of the pupil, a maximum area of the pupil, a minimum area of the pupil, a mean area of the pupil, the time to 75% recovery of pupil size, the time to 100% recovery of pupil size, and the area under the curve of the pupillary light reflex.

According to an embodiment, the secondary data 134 can include, for instance, a frequency spectrum. The frequency spectrum can be derived from the pupillary data via frequency-based transform methods. Such frequency-based transform methods may be a fast Fourier transform and the like, as would be understood by one of ordinary skill in the art. From the frequency spectrum, parameters such as an amplitude at a specific frequency or a band power across a range of frequencies, wherein the specific frequency or range of frequencies are correlated with a level of activity of a pathology, can be determined. Moreover, the frequency spectrum may be evaluated write large, wherein a mathematical model of the frequency spectrum is correlated with a level of activity of a pathology. To this end, heuristic models can be used in the development of algorithms.

Figure 5:
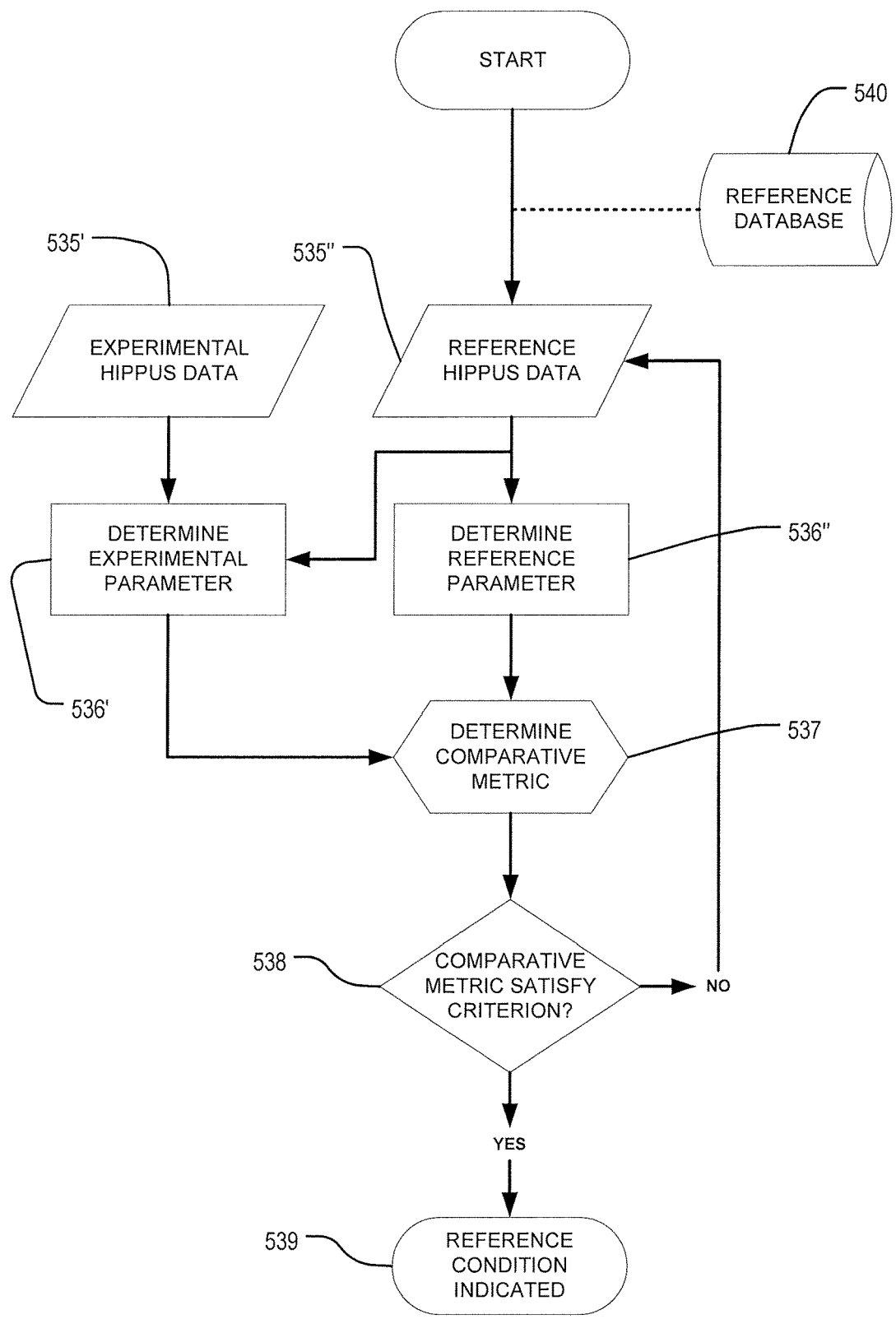
FIG. 5 is a flow diagram describing evaluation of a spectral analysis, according to an exemplary embodiment of the present disclosure.

During implementation of the above-described methods, and referring now to FIG. 5, selected parameters can be determined for experimental and reference data and compared such that the presence and/or quantity of a substance, drug, or physiologic substance can be determined.

To this end, first, reference hippus data 535" can be acquired from a reference database 540 and experimental hippus data 535' can be acquired, for example, from a current patient. This hippus data is analogous to the processed hippus data of FIG. 1, wherein the method of FIG. 1 has been applied to an acquired video sequence.

Having acquired appropriate hippus data, a first parameter, or experimental parameter 536', can be determined from the experimental hippus data 535' of a pupillary hippus of the patient. The experimental parameter 536' can be, but is not limited to, amplitude, frequency, band power, and a mathematical model of the waveform, as described above. Additionally, the experimental parameter 536' can be, among others, baseline pupil size, maximum pupil size, minimum pupil size, velocity of constriction (average constriction velocity and maximum constriction velocity), latency of constriction, velocity of re-dilation, maximum change in size of the pupil, maximum velocity of re-dilation of the pupil, mean velocity of re-dilation of the pupil, maximum area of the pupil, minimum area of the pupil, mean area of the pupil, time to 75% recovery of pupil size, time to 100% recovery of pupil size, and area under the curve of the pupillary light reflex.

Similarly to the above, a first parameter, or reference parameter 536", can be determined from reference hippus data 535" of a pupillary hippus of a reference patient or a representative pupillary hippus of a population of patients. The reference parameter 536" can be, but is not limited to, amplitude, frequency, band power, and a mathematical model of the waveform, as described above. Additionally, the experimental parameter 536' can be, among others, baseline pupil size, maximum pupil size, minimum pupil size, velocity of constriction (average constriction velocity and maximum constriction velocity), latency of constriction, velocity of re-dilation, maximum change in size of the pupil, maximum velocity of re-dilation of the pupil, mean velocity of re-dilation of the pupil, maximum area of the pupil, minimum area of the pupil, mean area of the pupil, time to 75% recovery of pupil size, time to 100% recovery of pupil size, and area under the curve of the pupillary light reflex.

In an exemplary embodiment, a second parameter, or comparative metric 537, can be determined as a computation based upon the experimental parameter 537' and the reference parameter 537" determined from the pupillary hippus of the patient and the pupillary hippus of the reference patient, for example, respectively. The comparative metric can include, among others, delta band power, or the difference between the band power of the experimental data and a corresponding band power of the reference data, % delta band power, normalized delta band power, and a similarity ratio between mathematical models of the experimental data and the reference data.

In an embodiment, the comparative metric 537 can be a correlation of an experimental waveform and a reference waveform, wherein a lack of correlation of the respective waveforms can be indicative or not of a physiologic condition.

Following determination of the comparative metric 537, according to an embodiment, the comparative metric 537 can be evaluated 538 with respect to a pre-determined threshold to determine the presence or absence of a biologically-active substance, a drug, or a physiologic perturbation.

The biologically-active substance, the drug, or the physiologic perturbation, as defined by the comparative metric evaluated, can then be indicated via a display.

For example, a patient may be suspected of recreational use of THC. If delta band power is the comparative metric and, over a frequency range associated with THC users, is determined to be significantly large when comparing the patient's data with reference data of a THC user, it can be determined that the patient has had an acute exposure to THC.

According to an embodiment, following the evaluation of the comparative metric with respect to a selected criterion 538, the outcome or, physiologic condition, can be displayed 539 via a display of the device described with reference to FIG. 7 such that a user can be alerted of the patient's condition, normal or otherwise.

Evaluation of the comparative metric relative to a criterion may reflect analysis of patterns and correlations of quantified frequency spectra that may be predictive of particular scenarios. The patterns and correlations may further predictive of interactions of drugs and their impact on pupillary hippus. According to an embodiment, these patterns and correlations can be identified by comparison against a library of frequency spectra associated with specific biologically-active compounds or drugs, a panel of specific biologically-active compounds or drugs, or multiple, interacting biologically-active compounds or drugs.

As discussed with respect to FIG. 5, comparisons of unknown, or experimental data, and reference data can be conducted by evaluating, for example, amplitudes at one or more, or a set of, specific frequencies along the frequency domain.

Figure 6:
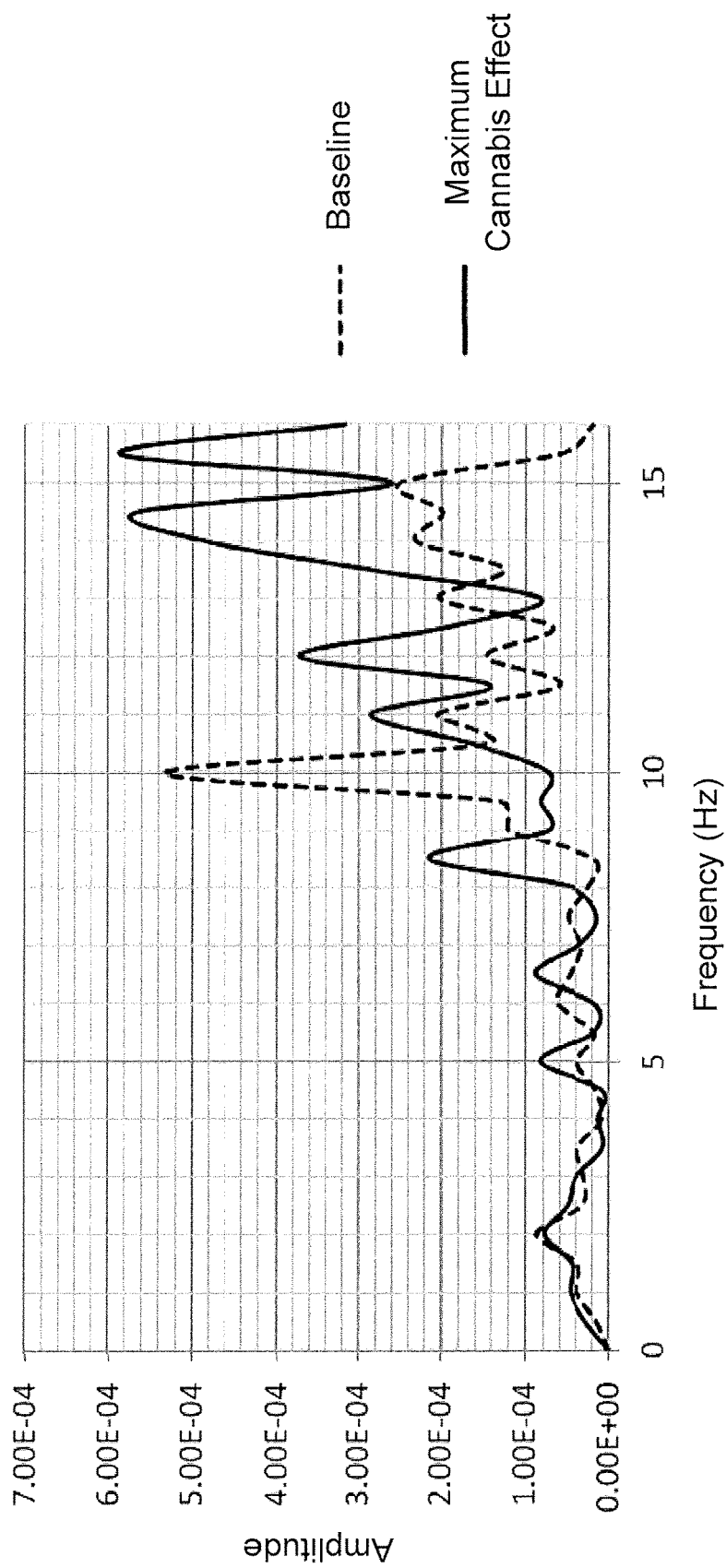
FIG. 6 is a graphical representation of a spectral analysis of hippus, according to an exemplary embodiment of the present disclosure.

Accordingly, FIG. 6 provides a graphical representation of a spectral evaluation of experimental hippus data and reference hippus data, as would be performed during the generation of secondary data in FIG. 1. As shown, experimental hippus data, captured at a time period of 'maximum cannabis effect' is illustrated alongside reference data displayed as a 'baseline'. The impact of cannabis use can be observed at varying frequencies across a spectrum for a single patient and attendant analysis of parasympathetic and sympathetic actions can be inferred therefrom. As observed in FIG. 6, for instance, cannabis use modifies high frequency pupillary oscillations (e.g., >10 Hz), indicative of increased sympathetic tone, compared to baseline, in response to cannabis exposure. In an example, the identification of physiologic perturbations could be performed by evaluation of a correlation between mathematical models of the plotted data, the correlation being a comparative metric and the mathematical models being selected parameters.

According to an embodiment, unknown frequency spectra from experimental hippus data may be analyzed, or filtered, with respect to a specific target biologically-active compound, such as THC, that may have increased amplitude between 12 Hz and 14 Hz along the frequency domain. Through determination of the area under the curve between these two frequencies, or band power, the unknown frequency spectra data may be compared to reference frequency spectra data to determine a delta band power. The delta band power, as discussed with respect to FIG. 6, can be a comparative metric or second parameter and, if present, the delta band power may be above a pre-determined threshold according to the sensitivity of the data acquisition equipment. In another embodiment, comparisons of complete pupillary responses in the frequency domain can be compared to the library of frequency spectra via pattern recognition techniques employed in machine learning for determining irregularities in data. This approach can identify one or more amplitude inflection points in the frequency domain that correlate to one or more known biologically-active compounds, drugs, such as THC, or physiologic conditions.

Complementary to the above approaches, and as suggested above, each unknown frequency spectra can be analyzed with respect to the effects of multiple, interacting biologically-active compounds, providing context to the impact of drug-drug interactions on the nervous system. For example, an unknown frequency spectra data may be filtered in the targeted context of the pupillary effects of the interaction of alcohol and THC. Moreover, when compared against a library of reference hippus data, it may be determined that one or more drug-drug interactions, correlated with physical perturbations of the pupillary light reflex, are present in the unknown frequency spectra data.

According to an embodiment, unknown and quantified frequency spectra data can be evaluated ad hoc to detect the presence of a biologically-active compound, as compared to a baseline. This approach may be useful when merely the presence of a specific biologically-active compound is in question. In an embodiment, the baseline can be established from a library a reference data of a variety of control patients, a prior control dataset of the same patient, or a combination thereof. According to an embodiment of the present disclosure, this approach can be applied to the detection and quantification of THC.

Further to the above, according to an embodiment, the present method can be used to detect dysautonomias, which include a variety of conditions including diabetic neuropathy and postural orthostatic tachycardia syndrome.

The method of the present embodiments can also be used for management of drug use and monitoring thereof. Currently, drug dose management is subjective according to clinician judgment. The approach of the present disclosure can be applied to long-term or repeated drug monitoring, including the detection of biologically-active compounds and respective, subsequent metabolites. Drug use and impairment with time, including dose response effects, can be observed per the method of the present disclosure, in particularly as it relates to THC. Metrics determined therein can be used clinically for objective analyses.

Moreover, the method can be developed to work as triage test in drivers suspected to be under the influence of alcohol or controlled substances. If there are any spectra unique to illegal substances discovered during the test, the driver will be submitted to other tests.

In addition to the above, the method of the present embodiments can be further implemented for the monitoring of post-surgery sedation of surgical patients.

According to an embodiment, the method of the present embodiments can also be used to discriminate between direct drug effects on the pupil vs. analgesic impact, (i.e., the method allows for the discrimination of drug vs. system-dependent parameters by using elements of static or dynamic pupil parameters as analogues of pharmacokinetics and area under the curve of the pupillary reflex dilation as the analogue of analgesic pharmacodynamics. The fast Fourier transform-derived "signature" of the present disclosure provides a non-invasive approach for further informing this paradigm by indicating the presence of a substance.

In an embodiment, the method of the present disclosure can be used in the context of analgesic response or other drug effects when combined with other features of the pupillary response including, but not limited to, the pupillary light reflex and the neurospecific neurostimulus-induced pupillary light reflex. This approach allows for isolation of drug-induced hyperalgesia, or a state of exposure-mediated nociceptive sensitization, from increased pain sensitivity resulting from injury or disease progression.

In an embodiment, the method of the present disclosure can be applied to the detection of THC tolerance and THC-induced hyperalgesia. The present embodiments can also be used to detect if a patient is responsive to THC therapy. A method of the present disclosure includes THC efficacy tracking for the identification of specific phenotypes based on pupillary changes, thereby allowing for individualized treatments.

According to an embodiment, the method of the present disclosure can be developed as a triage test for drivers suspected of being under the influence of alcohol or other controlled substances. If there are any spectra unique to illegal substances identified during the test, the driver can be submitted to other tests. In an embodiment, the method can be employed for drivers suspected of being under the influence of THC, wherein, if there are any spectra unique to THC discovered during the test, the driver can be submitted to other tests.

Next, a hardware description of an apparatus, or device, employing a method according to exemplary embodiments is described with reference to FIG. 7. In FIG. 7, the device includes a CPU 700 which perform is the processes described above. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device communicates, such as a server or computer.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

The hardware elements in order to achieve the device may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

Figure 7:
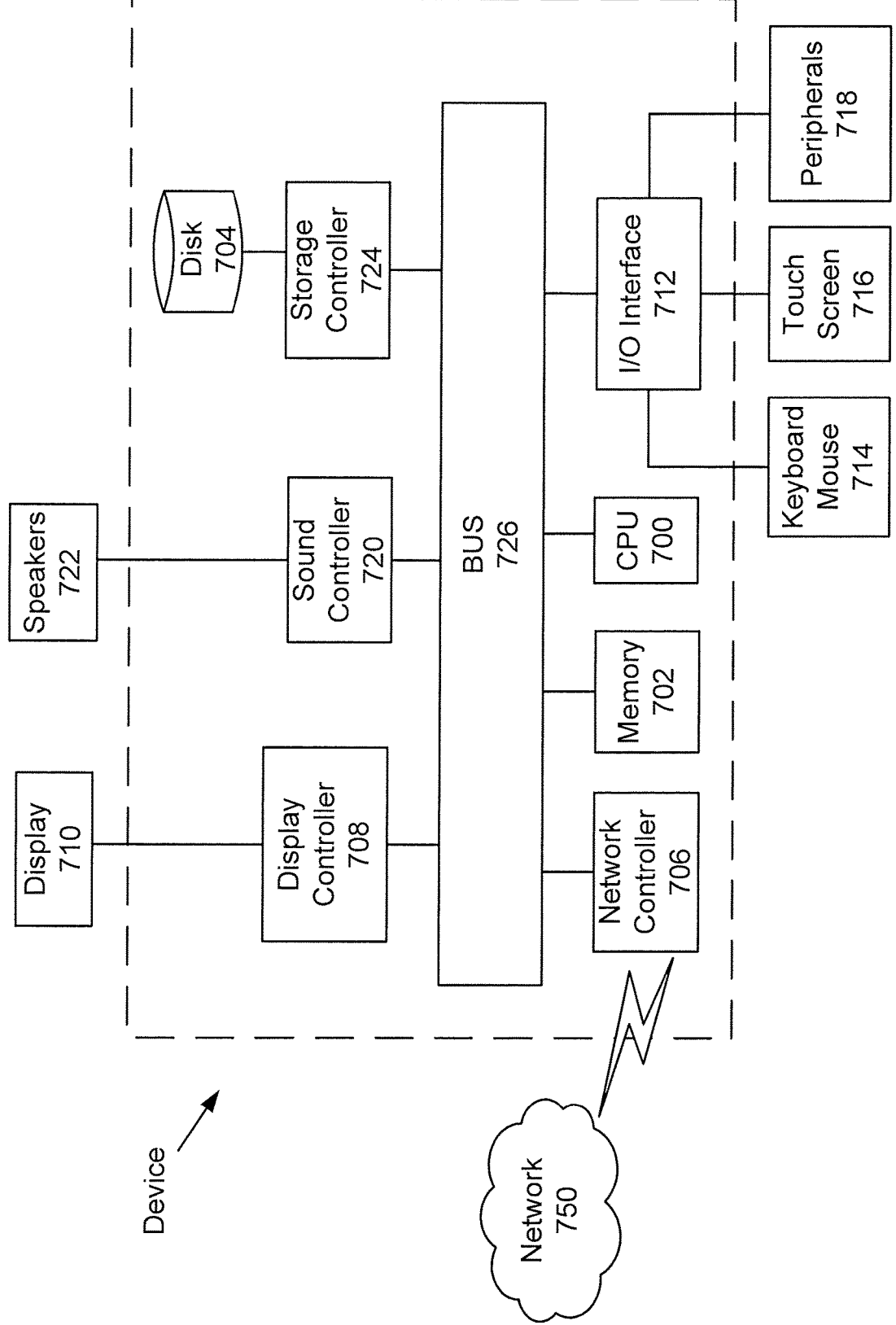
FIG. 7 is a hardware description of a device, according to an exemplary embodiment of the present disclosure.

The device in FIG. 7 also includes a network controller 706, such as an Intel Ethernet PRO network interface card from Intel Corporation of America, for interfacing with network 750. As can be appreciated, the network 750 can be a public network, such as the Internet, or a private network such as an LAN or WAN network, or any combination thereof and can also include PSTN or ISDN sub-networks. The network 750 can also be wired, such as an Ethernet network, or can be wireless such as a cellular network including EDGE, 3G and 4G wireless cellular systems. The wireless network can also be WiFi, Bluetooth, or any other wireless form of communication that is known.

The device further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the device, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the device. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) An apparatus for evaluation of a pupillary hippus of a patient, comprising a display, and processing circuitry configured to transform experimental data of the pupillary hippus of the patient and reference data via frequency-based transformation, calculate a first parameter of one or more selected parameters based upon the transformed experimental data of the pupillary hippus of the patient, calculate, based upon the transformed reference data, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of $\Delta^9$-tetrahydrocannabinol as the biologically-active target.

(2) The apparatus according to (1), wherein the processing circuitry is further configured to determine a level of impairment based upon the identification of $\Delta^9$-tetrahydrocannabinol as the biologically-active target and the first parameter.

(3) The apparatus according to either (1) or (2), wherein the processing circuitry is further configured to determine whether the generated metric achieves the predetermined threshold based upon a correlation between the first parameter of the experimental data and the corresponding first parameter of the reference data.

(4) The apparatus according to any of (1) to (3), wherein the first parameter based upon the experimental data is an amplitude at a predetermined frequency.

(5) The apparatus according to any of (1) to (4), wherein the first parameter based upon the experimental data is band power.

(6) The apparatus according to any of (1) to (5), wherein the generated metric is a difference between a band power of the experimental data and a band power of the reference data.

(7) The apparatus according to any of (1) to (6), wherein the first parameter based upon the experimental data is a mathematical model of the experimental data.

(8) The apparatus according to any of (1) to (7), wherein the first parameter based upon the experimental data is a mathematical model of a frequency spectrum of the experimental data.

(9) The apparatus according to any of (1) to (8), wherein the generated metric is a similarity ratio of mathematical models of a frequency spectrum of the experimental data and of the reference data.

(10) The apparatus according to any of (1) to (9), wherein the processing circuitry is further configured to acquire a plurality of video sequences of an eye of the patient, generate pupillary data based upon primary data calculated from the plurality of video sequences, the primary data including time-based pupillary dimensions, and calculate, from the generated pupillary data, secondary data, wherein the secondary data include the frequency spectrum of the pupillary hippus.

(11) The apparatus according to any of (1) to (10), wherein the primary data are calculated based upon a mask image, the processing circuitry, in order to generate the mask image, being further configured to locate a center of a pupil of the eye, a boundary of the pupil of the eye, and an iris of the eye, and generate the mask image, the mask image corresponding to an expected location of the iris based upon the location of the center of the pupil of the eye, the boundary of the pupil of the eye, and the iris of the eye.

(12) An apparatus for evaluation of a pupillary hippus of a patient, comprising a display, and processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of $\Delta^9$ tetrahydrocannabinol as the biologically-active target.

(13) The apparatus according to (12), wherein the processing circuitry is further configured to determine whether the generated metric achieves the predetermined threshold based upon a correlation between the first parameter of the experimental data and the corresponding first parameter of the reference data.

(14) The apparatus according to either (12) or (13), wherein the first parameter based upon the experimental data is an amplitude at a predetermined frequency.

(15) The apparatus according to any of (12) to (14), wherein the generated metric is a difference between a band power of the experimental data and a band power of the reference data.

(16) The apparatus according to any of (12) to (15), wherein the first parameter based upon the experimental data is a mathematical model of the experimental data.

(17) The apparatus according to any of (12) to (16), wherein the generated metric is a similarity ratio of mathematical models of a frequency spectrum of the experimental data and of the reference data.

(18) The apparatus according to any of (12) to (17), wherein the processing circuitry is further configured to acquire a plurality of video sequences of an eye of the patient, generate pupillary data based upon primary data calculated from the plurality of video sequences, the primary data including time-based pupillary dimensions, and calculate, from the generated pupillary data, secondary data, wherein the secondary data include the frequency spectrum of the pupillary hippus.

(19) The apparatus according to any of (12) to (18), wherein the primary data are calculated based upon a mask image, the processing circuitry, in order to generate the mask image, being further configured to locate a center of a pupil of the eye, a boundary of the pupil of the eye, and an iris of the eye, and generate the mask image, the mask image corresponding to an expected location of the iris based upon the location of the center of the pupil of the eye, the boundary of the pupil of the eye, and the iris of the eye.

(20) An apparatus for evaluation of a pupillary hippus of a patient, comprising processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on a display and based upon the determination, the evaluation of the pupillary hippus of the patient.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for evaluation of a pupillary hippus of a patient, comprising:
   a display; and
   processing circuitry configured to
      transform experimental data of the pupillary hippus of the patient and reference data via frequency-based transformation,
      calculate a first parameter of one or more selected parameters based upon the transformed experimental data of the pupillary hippus of the patient,
      calculate, based upon the transformed reference data, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of $\Delta^9$-tetrahydrocannabinol as the biologically-active target, wherein the first parameter based upon the experimental data is:

an amplitude at a predetermined frequency, band power, or a mathematical model of the experimental data.

2. The apparatus according to claim 1, wherein the processing circuitry is further configured to determine a level of impairment based upon the identification of $\Delta^9$-tetrahydrocannabinol as the biologically-active target and the first parameter.

3. The apparatus according to claim 1, wherein the processing circuitry is further configured to determine whether the generated metric achieves the predetermined threshold based upon a correlation between the first parameter of the experimental data and the corresponding first parameter of the reference data.

4. The apparatus according to claim 1, wherein the generated metric is a difference between a band power of the experimental data and a band power of the reference data.

5. The apparatus according to claim 1, wherein when the first parameter based upon the experimental data is the mathematical model, the mathematical model is of a frequency spectrum of the experimental data.

6. The apparatus according to claim 1, wherein the generated metric is a similarity ratio of mathematical models of a frequency spectrum of the experimental data and of the reference data.

7. The apparatus according to claim 1, wherein the processing circuitry is further configured to acquire a plurality of video sequences of an eye of the patient, generate pupillary data based upon primary data calculated from the plurality of video sequences, the primary data including time-based pupillary dimensions, and calculate, from the generated pupillary data, secondary data, wherein the secondary data include the frequency spectrum of the pupillary hippus.

8. The apparatus according to claim 7, wherein the primary data are calculated based upon a mask image, the processing circuitry, in order to generate the mask image, being further configured to locate a center of a pupil of the eye, a boundary of the pupil of the eye, and an iris of the eye, and generate the mask image, the mask image corresponding to an expected location of the iris based upon the location of the center of the pupil of the eye, the boundary of the pupil of the eye, and the iris of the eye.

9. An apparatus for evaluation of a pupillary hippus of a patient, comprising:

a display; and processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of $\Delta^9$-tetrahydrocannabinol as the biologically-active target, wherein the first parameter based upon the experimental data is:

an amplitude at a predetermined frequency, band power, or a mathematical model of the experimental data.

10. The apparatus according to claim 9, wherein the processing circuitry is further configured to determine whether the generated metric achieves the predetermined threshold based upon a correlation between the first parameter of the experimental data and the corresponding first parameter of the reference data.

11. The apparatus according to claim 9, wherein the generated metric is a difference between a band power of the experimental data and a band power of the reference data.

12. The apparatus according to claim 9, wherein the generated metric is a similarity ratio of mathematical models of a frequency spectrum of the experimental data and of the reference data.

13. The apparatus according to claim 9, wherein the processing circuitry is further configured to acquire a plurality of video sequences of an eye of the patient, generate pupillary data based upon primary data calculated from the plurality of video sequences, the primary data including time-based pupillary dimensions, and calculate, from the generated pupillary data, secondary data, wherein the secondary data include the frequency spectrum of the pupillary hippus.

14. The apparatus according to claim 13, wherein the primary data are calculated based upon a mask image, the processing circuitry, in order to generate the mask image, being further configured to locate a center of a pupil of the eye, a boundary of the pupil of the eye, and an iris of the eye, and generate the mask image, the mask image corresponding to an expected location of the iris based upon the location of the center of the pupil of the eye, the boundary of the pupil of the eye, and the iris of the eye.

15. An apparatus for evaluation of a pupillary hippus of a patient, comprising:

processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on a display and based upon the determination, the evaluation of the pupillary hippus of the patient, wherein the first parameter based upon the experimental data is:

an amplitude at a predetermined frequency, band power, or a mathematical model of the experimental data.

* * * * *